United States Patent [19]

Aoki

[11] 4,063,897
[45] Dec. 20, 1977

[54] SOLID ELECTROLYTE TYPE AIR-FUEL RATIO DETECTOR

[75] Inventor: Keiji Aoki, Susono, Japan

[73] Assignee: Toyota Jidosha Kogyo Kabushiki Kaisha, Toyota, Aichi, Japan

[21] Appl. No.: 693,629

[22] Filed: June 7, 1976

[30] Foreign Application Priority Data

Mar. 15, 1976 Japan .............................. 51-29771[U]

[51] Int. Cl.² ........................................... G01N 27/12
[52] U.S. Cl. ................................................. 23/254 E
[58] Field of Search ............. 23/254 E, 254 R, 255 R, 23/255 E, 232 R, 232 E, 232 C; 73/23, 23.1, 25, 26, 27 R

[56] References Cited

U.S. PATENT DOCUMENTS

| | | | |
|---|---|---|---|
| 1,918,702 | 7/1933 | Hebler et al. | 73/27 R |
| 2,782,103 | 2/1957 | Prentiss | 23/232 E X |
| 3,421,362 | 1/1969 | Schaeffer | 73/23 |

Primary Examiner—Robert M. Reese
Attorney, Agent, or Firm—Stevens, Davis, Miller & Mosher

[57] ABSTRACT

A solid electrolyte type air-fuel ratio detector comprising a housing fixed to the exhaust manifold of an engine and a detecting element disposed in the housing. The detecting element has a detecting portion projecting into the exhaust manifold so as to expose the detecting portion to the exhaust gas stream. The detecting portion is covered by a metallic cover for preventing the exhaust gas from directly impinging upon the detecting portion.

1 Claim, 2 Drawing Figures

SOLID ELECTROLYTE TYPE AIR-FUEL RATIO DETECTOR

DESCRIPTION OF THE INVENTION

The present invention relates to a solid electrolyte type air-fuel ratio detector for use in an internal combustion engine.

A solid electrolyte type air-fuel ratio detector (hereinafter referred to as an air-fuel ratio detector), called "λ-sensor", is used for detecting the concentration of oxygen in the exhaust gas from an internal combustion engine and for controlling the air-fuel ratio of the air-fuel mixture in the intake system in accordance with the detecting result of the air-fuel ratio detector. The air-fuel ratio detector is usually located in the exhaust gas stream so as to expose the detecting portion of the air-fuel ratio detector directly to impingement of the exhaust gas. The surface of the detecting portion which directly contacts with the exhaust gas stream is covered by a negative electrode comprised of a thin layer of platinum. Consequently, as is aforementioned, if the exhaust gas directly impinges upon the detecting portion, fine particles of iron and lead contained in the exhaust gas impinge upon the surface of the detecting portion, and causes the negative electrode to peel off. The resulting disadvantage is that the detecting ability of the air-fuel ratio detector is extremely reduced.

An object of the present invention is to eliminate the above disadvantage.

According to the present invention, there is provided a solid electrolyte type air-fuel ratio detector for use in an internal combustion engine having piping means for leading the exhaust gas from the engine cylinder to the atmosphere, said detector comprising a housing fixed to said piping means and a detecting element disposed in said housing, said detecting element being comprised of a solid electrolyte and having a detecting portion which projects into said piping means so as to expose the detecting portion to the exhaust gas stream, the outer surface of the detecting portion being covered by a thin layer of platinum, wherein the improvements comprise metallic means for covering the detecting portion of the detecting element, said metallic means having at least one hole arranged so that the exhaust gas flowing through said piping means diffuses into said metallic means through said hole and reaches to the outer surface of the detecting portion.

The above-mentioned object of the present invention may be more fully understood from the following descriptions of a preferred embodiment of the invention, together with the accompanying drawings.

DESCRIPTION OF A PREFERRED EMBODIMENT

Figure 1:
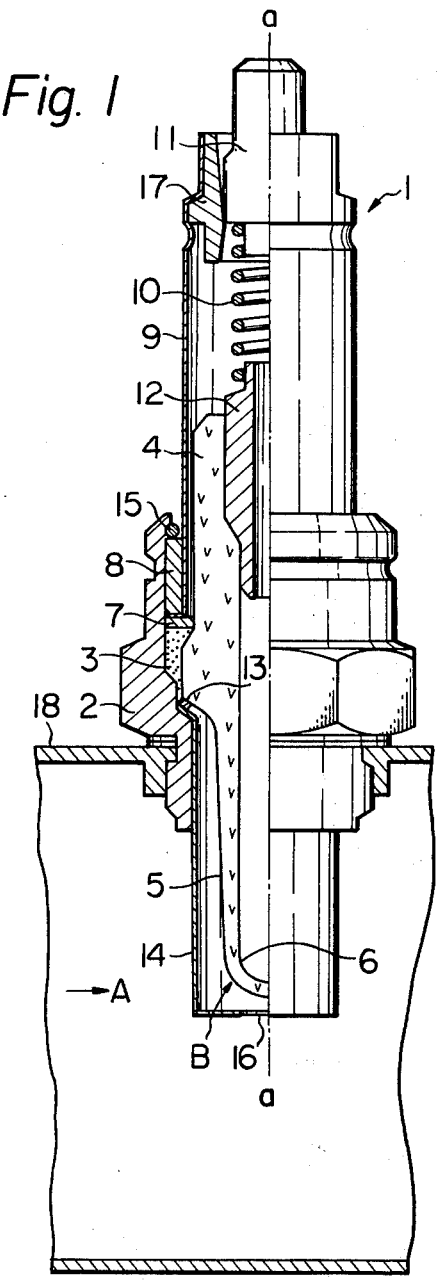
FIG. 1 is a side elevational view, partly in cross section, of an air-fuel ratio detector according to the present invention.

FIG. 1 shows an air-fuel ratio detector 1 according to the present invention. The air-fuel ratio detector 1 has a symmetrical construction with respect to the central axis a. Therefore, FIG. 1 shows a cross-sectional view of a half of the air-fuel ratio detector on the left side. The air-fuel ratio detector 1 comprises a housing 2, a solid electrolyte 4 comprised of, for example, zirconia ceramic and fixed to the housing 2 by means of adhesives 3, a negative electrode 5 comprised of a thin layer of platinum and covering the outer surface of the solid electrolyte 4, a positive electrode 6 comprised of a thin layer of platinum and covering the inner surface of the solid electrolyte 4, an outer case 9 having a flange interposed between spacers 7 and 8, a conductive member 12 one end of which contacts the positive electrode 6, the other end being connected to a positive terminal 11 via a conductive spring 10, an insulating member 17 interposed between the positive terminal 11 and the outer case 9, and a guard cover 14 according to the present invention, said guard cover 14 being fixed to the housing via a washer 13 by means of the solid electrolyte 4 and extending into the exhaust manifold 18 at right angles to the direction of gas flow therein. The spacer 8 is fixed to the housing 2 via a O ring 15 by inwardly bending the upper end of the housing 2. The air-fuel ratio detector 1 is screwed into the wall of the exhaust manifold 18 of the engine so as to detect the concentration of oxygen in the exhaust gas which flows in the exhaust manifold 18 in the direction of the arrow A.

Figure 2:
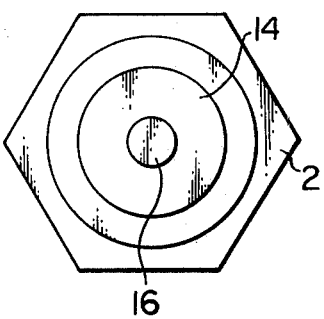
FIG. 2 is a bottom view of FIG. 1.

The guard cover 14 is made of a heat resistant impermeable material such as stainless steel and has on its lower end an exhaust gas introducing hole 16. The exhaust gas flowing in the exhaust manifold 18 turns 90° and diffused into the guard cover 14 through the exhaust gas introducing hole 16 and then reaches to the surface of the negative electrode 5. Consequently, the fine particles of iron and lead contained in the exhaust gas are obstructed by the guard cover 14 and, therefore, cannot directly impinge upon the detecting portion B, i.e, the negative electrode 5. In the embodiment shown in FIGS. 1 and 2, a single exhaust gas introducing hole 16 is formed on the guard cover 14. However, instead of this, a number of small holes can be formed on the guard cover 14.

Furthermore, the guard cover 14 according to the present invention can be applied to the air-fuel ratio detector in which the solid electrolyte 4 is comprised of titanic oxide ceramic.

According to the present invention, the negative electrode is prevented from peeling off, thus improving the life of the air-fuel ratio detector.

What is claimed is:

1. In a solid electrolyte type air-fuel ratio detector for use in an internal combustion engine having piping means for leading the exhaust gas from the engine cylinder to the atmosphere, said detector having a housing fixed to said piping means and a detecting element disposed in said housing, said detecting element having a solid electrolyte and a detecting portion which projects into said piping means so as to expose the detecting portion to the exhaust gas stream, the outer surface of the detecting portion being covered by a thin layer of platinum wherein the improvement comprises means for preventing the exhaust gas from directly impinging upon the detecting portion, said means comprising an impermeable metallic covering made of heat resistant material and disposed normal to the direction of exhaust gas flow for covering the detecting portion of the detecting elemenet, said covering having a lower end face disposed substantially parallel to the direction of the exhaust gas flow, and at least one hole formed in said lower end face for causing the exhaust gas to turn through 90° to diffuse to the outer surface of the detecting portion.

* * * * *